United States Patent
Lai et al.

(10) Patent No.: US 7,402,693 B2
(45) Date of Patent: Jul. 22, 2008

(54) CYCLOBUTANETETRACARBOXYLATE COMPOUND AND PREPARATION METHOD THEREOF

(75) Inventors: Ming-Chih Lai, Hsinchu County (TW); Chia-Wen Chang, Hsinchu County (TW); Chi-Wi Ong, Hsinchu County (TW)

(73) Assignee: Daxin Material Corporation, Hsinchu County (TW)

( * ) Notice: Subject to any disclaimer, the term of this patent is extended or adjusted under 35 U.S.C. 154(b) by 0 days.

(21) Appl. No.: 11/888,703

(22) Filed: Aug. 2, 2007

(65) Prior Publication Data

US 2008/0033199 A1 Feb. 7, 2008

Related U.S. Application Data

(63) Continuation-in-part of application No. 11/253,798, filed on Oct. 19, 2005, now abandoned.

(30) Foreign Application Priority Data

Oct. 20, 2004 (TW) .............................. 93131887 A

(51) Int. Cl.
 *C07C 69/74* (2006.01)
(52) U.S. Cl. ..................................... 560/123
(58) Field of Classification Search .................. 560/123
 See application file for complete search history.

(56) References Cited

U.S. PATENT DOCUMENTS 3,139,395 A 6/1964 Griffin

OTHER PUBLICATIONS

Buddrus et al., Distinction of symmetrically substituted carboxylic compounds, (Chemische Berichte, (1998), 121, (2) 295-297.
Shaikhrazieva et al., Photoinitiated addition of maleic anhydride (Zhurnal organicheskoi Khimii., (1972), 8 (2) 377-382.
Scharf et al., Tetracarbonylmolybdenum (Angewandte Chemie, International Edition, (1970), 9 (10) 810.
Maier et al., samll rings, 77 Generation and trapping of tetramethyl cyclobutadienetetracarboxylate (Chemische Berichte., (1993), 126, 1827-33.
Ohga et al., Photochemistry of alph, beta-unsaturated gamma-lactones (Bulletin of the chemical society of Japan (1970), 43 (11), 35-05-10.
Ding et al., Dongbei Shida Xuebao (Ziran Kexueban (2001), 33 (4) 61-65).

*Primary Examiner*—Jafar Parsa
(74) *Attorney, Agent, or Firm*—Jianq Chyun IP Office

(57) ABSTRACT

The invention provides a cyclobutanetetracarboxylate compound of general formula (I) and a preparation method thereof:

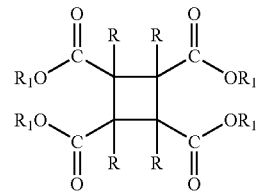

formula (I)

in which R and $R_1$ are as defined in the specification.

11 Claims, 2 Drawing Sheets

CYCLOBUTANETETRACARBOXYLATE COMPOUND AND PREPARATION METHOD THEREOF

This application is a continuation-in-part of application Ser. No. 11/253,798 filed on Oct. 19, 2005 now abandoned, claims the benefit thereof and incorporates the same by reference.

BACKGROUND OF THE INVENTION

1. Field of the Invention

The present invention relates to a cyclobutanetetracarboxylate compound and a preparation method thereof.

2. Description of the Prior Art

Cyclobutanetetracarboxylic dianhydrides are important monomer materials for the preparation of an alignment film useful for flat panel displays. Japanese Laid-open Hei 2003-192685 discloses a process for producing cyclobutanetetracarboxylic dianhydride comprising irradiating maleic anhydride to synthesize the cyclobutanetetracarboxylic dianhydride. This process, however, suffers from the shortcomings of a low yield in the production of the butane structure.

To overcome the above shortcomings, the inventors of the subject application developed a new synthesis route comprising synthesizing a cyclobutanetetracarboxylate, hydrolyzing the cyclobutanetetracarboxylate, and dehydrating the hydrolyzed product to obtain the corresponding cyclobutanetetracarboxylic dianhydride. The new route according to the present invention achieves an improved yield of the desired compounds.

SUMMARY OF THE INVENTION

One of the objects of the invention is to provide a cyclobutanetetracarboxylate compound.

Another object of the invention is to provide a process for preparing the cyclobutanetetracarboxylate compound.

DETAILED DESCRIPTION OF THE INVENTION

Figure 1:
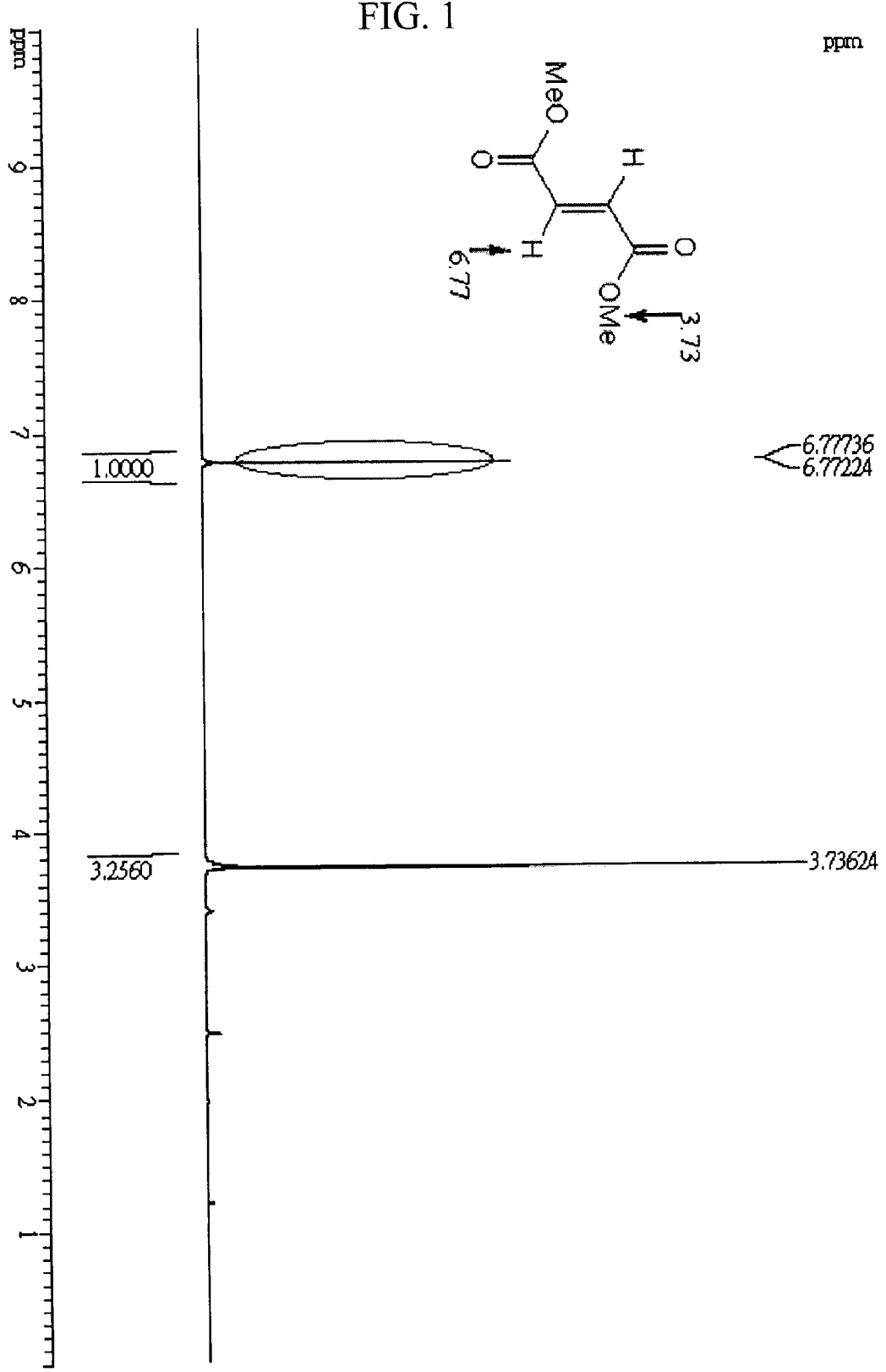
FIG. 1 is the NMR spectrum obtained before the cyclization reaction in the example.

The invention provides a cyclobutanetetracarboxylate compound of the general formula (I):

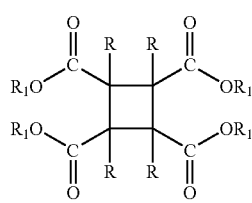

formula (I)

in which:

R can be the same or R is different from each other and independently represents hydrogen or a halogen or a monovalent organic radical; and $R_1$ is a $C_1$-$C_4$ alkyl.

There are no special requirements for the species of the monovalent organic radical suitable for the present invention. Preferably, the monovalent organic radical is a $C_1$-$C_4$ alkyl, which can be straight-chained or branched, or a $C_3$-$C_4$ cyclic alkyl; and more preferably, is methyl, ethyl, propyl, isopropyl, butyl, or isobutyl.

The invention further provides a process for preparing the cyclobutanetetracarboxylate compound of formula (I). The inventive process comprises the steps of:

(a) conducting an esterification reaction of a diacid compound of general formula (II)

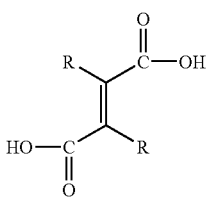

formula (II)

(in which R is as defined hereinbefore) with an alcohol of general formula (III)

$R_1$—OH    formula (III)

in the presence of an acidic solvent to obtain a precursor compound of general formula (IV)

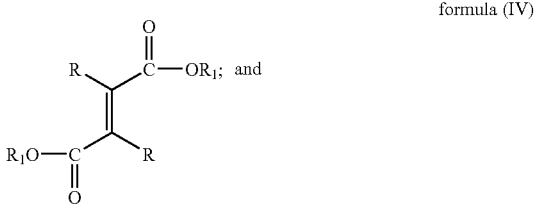

formula (IV)

(b) conducting a cyclization reaction by irradiating the precursor compound of general formula (IV) with an energy ray in a solvent in which the compound of formula (IV) is insoluble or difficult to be dissolved, to obtain the cyclobutanetetracarboxylate compound of general formula (I).

The acidic solvent used in the inventive process can also be used as a catalyst to enhance the reaction rate.—Suitable acidic solvent can be a mono-protonic inorganic acid, a multi-protonic inorganic acid, or an organic acid, which preferably is hydrochloric acid or sulfuric acid.

The suitable species of the alcohol in the esterification reaction step (a) will vary with the desired product to be obtained and may include, for example, methanol, ethanol, propanol, or isopropanol. The diacid compound used in the present invention is a fumaric acid. The esterification reaction is conducted at a temperature ranging from 60 to 110° C. for 2 to 20 hours.

The energy ray used in step (b) of the inventive process refers to a light source with a wavelength of from 200 to 600 nm, preferably an ultraviolet light. In general, the irradiation time will vary with the wavelength of the energy ray and is normally in the range of from about 30 minutes to 30 hours. In addition, since the solvent used in step (b) renders the compound of formula (IV) insoluble or difficult to be dissolved, the compound of formula (IV) can be dispersed or suspended in the solvent so that the cyclization reaction of the compound of formula (IV) can be performed more effectively, thereby increasing the yield of the reaction. Examples of such solvent include methanol, ethanol, water, or a mixture thereof.

In step (b), the temperature of the solution will increase when the cyclization reaction is conducted with irradiation of an ultraviolet light. The elevated temperature of the solution increases the reverse reaction rate of step (b) so that the yield is decreased. Therefore, the yield of the reaction can be effectively increased by controlling the reaction temperature of step (b) at 1 to 15° C.

The compound of formula (I) according to the present invention can be catalytically hydrolyzed in the presence of an acid or a base in a conventional manner known to persons skilled in the art to form the corresponding cyclobutanetetracarboxylic acid, which can be further dehydrated to form the corresponding cyclobutanetetracarboxylic dianhydride.

The present invention will be further described in the following example. However, the example will not make any limitations to the scope of the invention. Any modifications or alterations on the invention that can be easily accomplished by persons skilled in the art are encompassed in the disclosure of the specification and the accompanying claims.

EXAMPLE

Synthesis of a Cyclobutanetetracarboxylic Dianhydride

In a 5-liter flask, methanol (3000 ml, 75 mol) and then fumaric acid (1160 g, 10 mol) and concentrated sulfuric acid (10 ml, 0.2 mol) were added. The reaction was conducted at a controlled temperature of 75° C. for 10 hours and then cooled to room temperature. The resultant solid was collected by vacuum filtration and washed with methanol to obtain dimethyl fumarate (1224 g, 8.5 mol).

Figure 2:
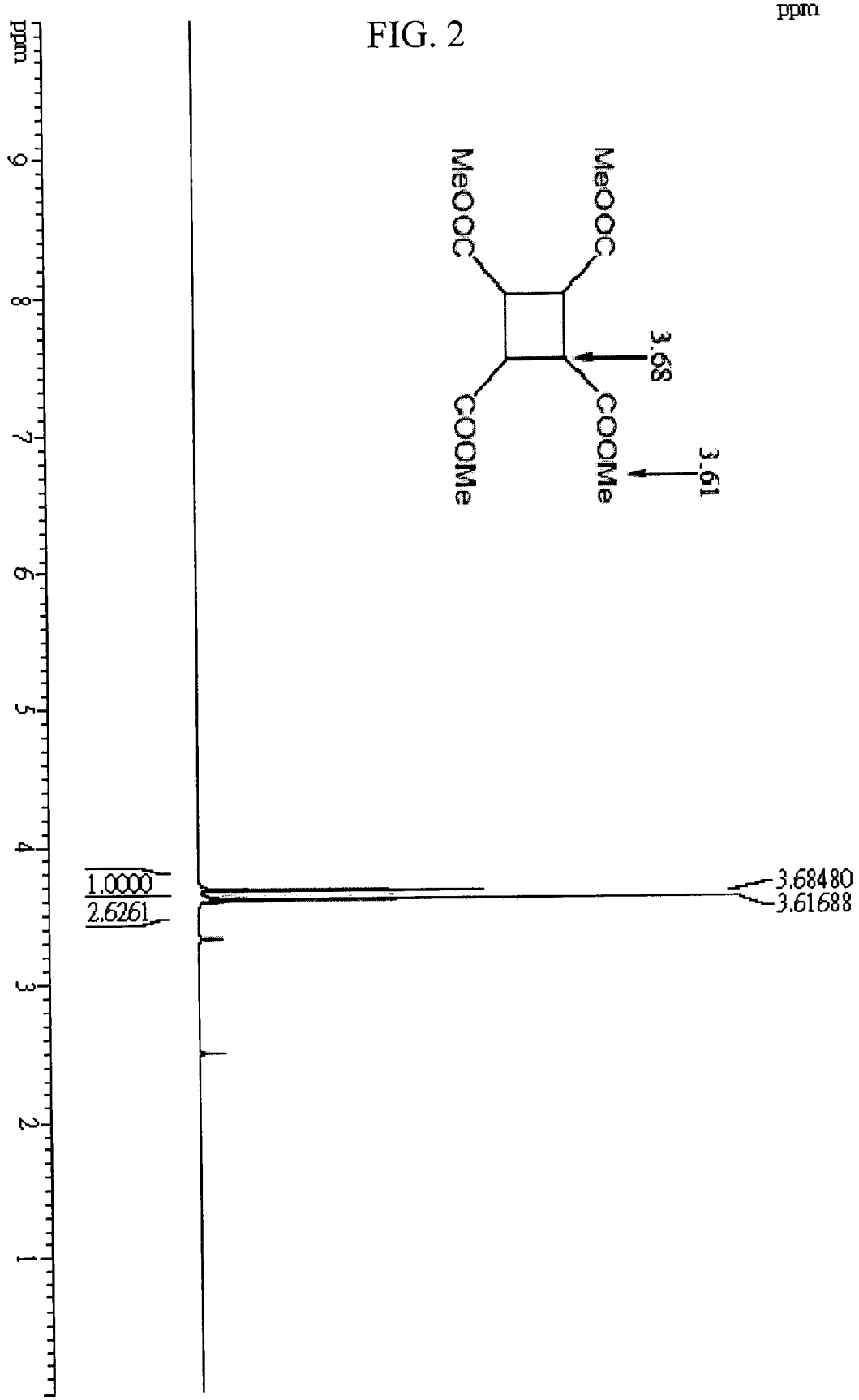
FIG. 2 is the NMR spectrum obtained after the cyclization reaction in the example.

The dimethyl fumarate (1224 g, 8.5 mol) and water (4000 ml) were added to a 6-liter flask and irradiated by 365 nm ultraviolet lights at a temperature from 5 to 7° C. for 7 hours. The resultant solid in the flask was vacuum filtered to obtain tetramethyl cyclobutane-1,2,3,4-tetracarboxylate (1224 g, 4.25 mol). According to the NMR spectrum as shown in FIG. 1, dimethyl fumarate was present before the cyclization reaction. It can be observed from FIG. 2 that, after the cyclization reaction, the absorption peak at 6.77 ppm disappeared which means that dimethyl fumarate had been reacted completely. The absorption peak at 3.68 ppm represents the generation of the corresponding cyclobutanetetracarboxylate. FIGS. 1 and 2 prove that the yield of the reaction is almost 100%.

The resultant tetramethyl cyclobutane-1,2,3,4-tetracarboxylate (1224 g, 4.25 mol) and aqueous hydrochloric acid (3000 ml) were added to a 5-liter flask; reacted at a controlled temperature of 85° C. for 24 hours; cooled to room temperature; concentrated; and dried to obtain cyclobutane-1,2,3,4-tetracarboxylic acid (870 g, 3.75 mol).

The cyclobutane-1,2,3,4-tetracarboxylic acid (501 g, 2.16 mol) and acetic anhydride (3000 ml) were added to a 5-liter flask and reacted at a controlled temperature of 150° C. for 24 hours. The reaction was cooled to room temperature; concentrated; and dried to obtain 1,2,3,4-cyclobutanetetracarboxylic dianhydride (573 g, 2.93 mol).

What is claimed is:

1. A process for the preparation of a cyclobutanetetracarboxylate compound of formula I

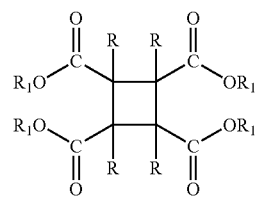

formula I in which:
R can be the same or R is different from each other and independently represents hydrogen or a halogen or a monovalent organic radical; and $R_1$ is a $C_1$-$C_4$ alkyl, comprising:
conducting a cyclization reaction by irradiating a precursor compound of general formula (IV)

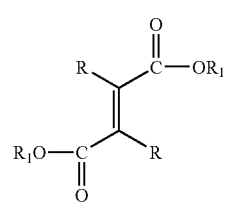

formula (IV)

with an energy ray in a solvent in which the compound of formula (IV) is insoluble or difficult to be dissolved, to obtain the cyclobutanetetracarboxylate compound of general formula (I).

2. The process of claim 1, wherein the cyclization reaction is conducted at a temperature from 1 to 15° C.

3. The process of claim 1, wherein the energy ray used in step (b) is a light source having a wavelength of from 200 to 600 nm.

4. The process of claim 1, wherein the energy ray used in step (b) is an ultraviolet light.

5. The process of claim 1, wherein the cyclization reaction is conducted for 30 minutes to 30 hours.

6. The process of claim 1, wherein less than 5 parts by weight of the compound of formula (IV) is dissolved in 100 parts by weight of the solvent.

7. The process of claim 1, wherein the solvent is selected from the group consisting of ethanol, water, methanol, and a mixture thereof.

8. The process of claim 1, further comprising:
conducting an esterification reaction of a diacid compound of general formula (II)

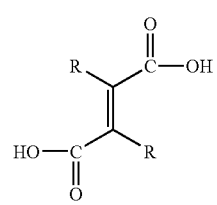

formula (II)

(in which R is defined hereinbefore) with an alcohol of general formula (III)

$R_1$—OH    formula (III)

in the presence of an acidic solvent to obtain the precursor compound of general formula (IV).

9. The process of claim 7, wherein the alcohol of general formula (III) is methanol, ethanol, propanol, or isopropanol.

10. The process of claim 7, wherein the esterification reaction is conducted at a temperature from 60 to 110° C.

11. The process of claim 7, wherein the esterification reaction is conducted for 2 to 20 hours.

* * * * *